(12) United States Patent
Gleich

(10) Patent No.: US 7,778,681 B2
(45) Date of Patent: *Aug. 17, 2010

(54) METHOD OF DETERMINING THE SPATIAL DISTRIBUTION OF MAGNETIC PARTICLES

(75) Inventor: Bernhard Gleich, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1855 days.

This patent is subject to a terminal disclaimer.

(21) Appl. No.: 10/270,991

(22) Filed: Oct. 15, 2002

(65) Prior Publication Data

US 2003/0085703 A1 May 8, 2003

(30) Foreign Application Priority Data

Oct. 19, 2001 (DE) ................. 101 51 778

(51) Int. Cl.
*A61B 5/05* (2006.01)
(52) U.S. Cl. .................. 600/407; 600/410; 600/420; 600/424; 600/409; 607/103; 324/300; 324/307; 324/309
(58) Field of Classification Search ............... 424/9.32, 424/451; 128/899; 600/407–409, 410, 420, 600/12, 424; 324/301, 302, 200–263, 307, 324/309, 300; 606/27; 607/103
See application file for complete search history.

(56) References Cited

U.S. PATENT DOCUMENTS

| | | | | |
|---|---|---|---|---|
| 5,735,279 A | * | 4/1998 | Klaveness et al. | 600/409 |
| 6,082,366 A | * | 7/2000 | Andra et al. | 128/899 |
| 6,470,220 B1 | * | 10/2002 | Kraus et al. | 607/103 |

FOREIGN PATENT DOCUMENTS

| DE | 095124 A1 | * | 11/1983 |
|---|---|---|---|
| DE | 3940260 A1 | * | 12/1989 |

* cited by examiner

*Primary Examiner*—Brian Casler
*Assistant Examiner*—John F Ramirez

(57) ABSTRACT

The invention relates to a method of determining the spatial distribution of magnetic particles in an examination zone. According to this method a spatially inhomogeneous magnetic field is generated which includes at least one zone (301) in which the magnetization of the particles is in a non-saturated state whereas the particles in the remaining zone are in a saturated state. Shifting this zone within the examination zone produces a change of the magnetization which can be externally detected and contains information concerning the spatial distribution of the magnetic particles in the examination zone.

17 Claims, 5 Drawing Sheets

METHOD OF DETERMINING THE SPATIAL DISTRIBUTION OF MAGNETIC PARTICLES

Figure 1:
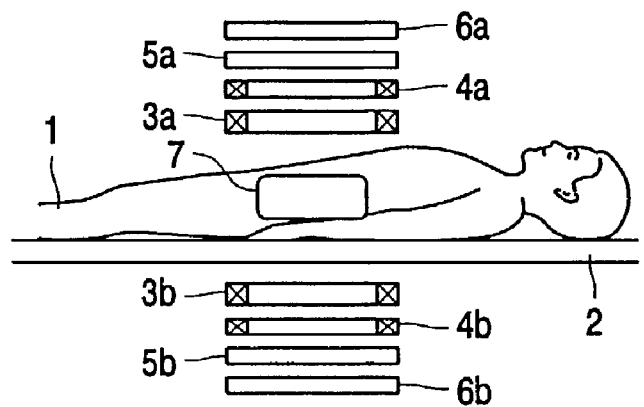

The invention relates to a method of determining the spatial distribution of magnetic particles in an examination zone. The invention also relates to the use of suitable magnetic particles for such a method and to an arrangement for carrying out the method.

Magnetic substances can be comparatively simply detected and can, therefore, be used in particular for medical examinations.

For example, DE-PS 19 532 676 discloses a method of determining the position of a magnetic marker in the gastro-intestinal tract. According to this method, a single magnetic marker, having a diameter of approximately 8 mm, is introduced into the gastro-intestinal tract. In order to track the progression of this marker in the gastro-intestinal tract, it is exposed to a pulsed external magnetic field of alternating polarity, in a given temporal sequence, so that the marker is repeatedly magnetized anew during its travel and its magnetic moment is oriented each time parallel to the external magnetic field again.

The secondary magnetic field originating from the marker is separately measured by means of anisotropic magnetic field sensors in the directions parallel and perpendicular to the axis of the coil generating the external magnetic field, the coil with the magnetic field sensors attached thereto being displaced until the magnetic field sensors deliver a zero signal. The position of the coil thus obtained is correlated to the position of the marker in the gastro-intestinal tract. The motion of the marker can thus be determined in conjunction with the instantaneous measuring instant. This method offers a low spatial and temporal resolution.

Also known are MR (MR=magnetic resonance) methods in which ferromagnetic or ferrimagnetic particles are injected into the blood stream of a patient in order to enhance the contrast of the blood vessels. The particles are so small (from 5 to 10 nm) that no Weiss zones can be formed therein. MR methods have the drawback of the high cost of an MR apparatus for carrying out the MR method. Such an MR apparatus inter alia requires a magnet which generates a uniform, steady magnetic field in the examination zone during the entire MR examination. In order to enable an adequate signal-to-noise ratio to be obtained, this magnetic field must have a strength of 0.5 Tesla or more. This necessitates the use of superconducting magnets.

It is an object of the present invention to provide a method of determining the spatial distribution of magnetic particles in an examination zone which offers a suitable temporal and spatial resolution and requires only a comparatively small amount of hardware for carrying out the method.

This object is achieved by means of a method of determining the spatial distribution of magnetic particles in an examination zone, which method in accordance with the invention includes the steps of:

a) generating a magnetic field having a magnetic field strength which varies in space in such a manner that a first sub-zone (301) having a low-magnetic field strength and a second sub-zone (302) having a high magnetic field strength are formed in the examination zone, b) changing the position in space of the two sub-zones in the examination zone in such a manner that the magnetization of the particles changes locally, c) acquiring signals which are dependent on the magnetization in the examination zone which has been influenced by the change of the position in space, d) evaluating the signals in order to extract information concerning the spatial distribution of the magnetic particles in the examination zone.

A spatially inhomogeneous magnetic field is generated in the examination zone in accordance with the invention. The magnetic field in the first sub-zone is so weak that the magnetization of the particles deviates more or less from the external magnetic field, which means that it is not saturated. This first sub-zone is preferably a spatially coherent zone; it may be a punctiform zone, but also a line or a surface. In the second sub-zone (that is, in the part of the examination zone outside the first sub-zone), the magnetic field is strong enough to keep the particles in a state of saturation. The magnetization is saturated when the magnetization of practically all particles is oriented approximately in the direction of the external magnetic field, so that when the strength of the magnetic field is further increased, the increase of the magnetization in this sub-zone will be less than that in the first sub-zone in response to a corresponding increase of the magnetic field.

When the position of the two sub-zones within the examination zone is changed, the (overall) magnetization in the examination zone changes. Therefore, when the magnetization is measured in the examination zone, or physical parameters influenced thereby are measured, information concerning the spatial distribution of the magnetic particles in the examination zone can be derived therefrom.

In practice the particles have non-identical magnetic properties. For example, a part of the particles may be in the saturated state at a given magnetic field strength, while another part is still in the non-saturated state. However, this results in an (additional) non-linearity of the magnetization characteristic, leading to a change of the magnetization in the examination zone when the position of the two sub-zones is changed.

One possibility for changing the position in space of the two sub-zones consists in shifting a coil system and/or permanent magnet system (or parts thereof), provided for generating the magnetic field, on the one side and the object to be examined on the other side relative to one another. This is a preferred method when very small objects have to be examined by means of very strong gradients (microscopy).

Claim 2, however, discloses an embodiment which does not require mechanical motions. The position in space of the two sub-zones can thus be comparatively quickly changed, offering additional advantages for the acquisition of signals which are dependent on the magnetization in the examination zone.

In the embodiment disclosed in claim 3 signals are acquired which are proportional to the variation in time of the magnetization in the examination zone. In order to ensure that these signals are as large as possible, it is important that the position in space of the two sub-zones in the examination zone is changed as quickly as possible. For the acquisition of these signals use can be made of a coil whereby a magnetic field is generated in the examination zone. However, preferably a separate coil is employed.

The changing of the position in space of the sub-zones can be initiated by means of a temporally variable magnetic field. To this end, a like-wise periodic signal is induced in a coil. The reception of this signal appears to be difficult, however, since the signals generated in the examination zone and the temporally variable signal are simultaneously active; therefore, it is not simply possible to discriminate between the signals induced by the magnetic field and the signals induced by the changing of the magnetization in the examination zone.

This problem is avoided in the embodiment disclosed in claim 4. This embodiment utilizes the fact that the frequency components of the second frequency band can arise exclusively as a result of a change of the magnetization in the examination zone which is due to the non-linearity of the magnetization characteristic. When the temporally variable magnetic field exhibits a sinusoidal periodic variation, the first frequency band consists of only a single frequency component, that is, the sinusoidal fundamental oscillation. The second frequency band, however, contains not only this fundamental oscillation, but also higher harmonics (so-called harmonic waves) of the sinusoidal fundamental oscillation which can be taken into account for the evaluation.

The magnetic particles suitable for the method in accordance with the invention should have dimensions which are small in comparison with the dimensions of the voxels whose magnetization is to be determined by means of the method in accordance with the invention. Furthermore, the magnetization of the particles should reach the saturated state in response to as weak as possible field strengths of the magnetic field. The lower the field strength required for this purpose, the higher the spatial resolution will be or the weaker the (external) magnetic field to be generated in the examination zone may be. Furthermore, the magnetic particles should have an as high as possible dipole moment or a high saturation induction in order to ensure that the changing of the magnetization yields as strong as possible output signals. When the method is used for medical examinations, moreover, it is important that the particles are not toxic.

In the embodiment as disclosed in claim 5 the particles are so small that only a single magnetic domain (a monodomain) can be formed or that no Weiss zones can arise therein. The dimensions of the particles should then be in the nanometer range. In the previously mentioned contrast agents for MR examinations these particles have a size of from 5 to 10 nm. This particle size is not yet optimum for the invention. When the particle dimensions are larger, smaller field strengths may suffice to ensure saturation of the magnetization of the particles. However, the dimensions should not be so large that several magnetic domains or Weiss zones can be formed in the particles. Therefore, suitable particle sizes are in a range of from 20 nm to approximately 800 nm, the upper limit also being dependent on the material. A material which is suitable for monodomain particles is, for example, magnetite ($Fe_3O_4$). Particles of this kind can be inhaled, for example, for examination of the lungs.

In the embodiment disclosed in claim 6, however, use is made of larger particles in which a number of magnetic domains may be formed. With a view to the spatial resolution, these particles should consist of a magnetic material which is saturated in the presence of a low magnetic field strength (implying a low saturation induction). This condition need not be satisfied in the further embodiment as disclosed in claim 7. Because the particles therein have only a thin layer of a magnetic material, magnetic saturation at a low field strength is ensured even when the layer does not consist of a material having a low saturation induction.

The embodiment as disclosed in claim 8 enables easy application of the particles in the case of medical examinations. When use is made of a dispersion with the monodomain particles in conformity with claim 5, this dispersion can be injected into the blood stream, for example, in order to image the vascular tree or the heart. This application is not toxic as is demonstrated by the use of said MR contrast agent. A dispersion with the particles defined in the claims 6 or 7 can be used for the examination of the gastro-intestinal tract after oral administration to a patient to be examined.

Generally speaking, it is advantageous when the particles have a low effective anisotropy (in this context and hereinafter the term "effective anisotropy" is to be understood to mean the magnetic anisotropy resulting from the shape anisotropy and the crystal anisotropy), because a change of its magnetization direction does not require rotation of these particles. Therefore, use can also be made of quickly varying magnetic fields, resulting in higher signal amplitudes and a more attractive signal-to-noise ratio. However, in the embodiment as disclosed in claim 9 use is made of the fact that in the case of particles having a sufficiently high effective anisotropy (for example, elongate particles) a change of the magnetization direction requires a mechanical rotation of the particles. The speed at which this change of direction can take place in a liquid medium is a measure of the viscosity in said medium.

An arrangement for carrying out the method in accordance with the invention is disclosed in claim 11. The preferred embodiment of this arrangement as disclosed in claim 12 is provided with a gradient coil system for generating the magnetic field in the examination zone. When the gradient coil system comprises, for example, two similar windings which are arranged to both sides of the examination zone but conduct oppositely directed currents (Maxwell coil), this magnetic field is zero in a point on the winding axis and increases substantially linearly with an opposed polarity to both sides of this point. The magnetization will not be saturated only in the particles which are situated at the area around said zero point of the field. The magnetization is in the state of saturation in the particles situated outside this area.

In the further embodiment as disclosed in claim 13, the zone created around the zero point of the field by the gradient coil system, that is, the first sub-zone, is shifted within the examination zone by the temporally variable magnetic field. In the case of a suitable variation in time and orientation of this magnetic field, the zero point of the field can thus traverse the entire examination zone.

The change of magnetization accompanying the shift of the zero point of the field can be detected in conformity with the further embodiment disclosed in claim 14. The coil used for the reception of the signals generated in the examination zone may then be a coil which already serves to generate a magnetic field in the examination zone. However, it is also advantageous to use a separate coil for the reception, because this coil can be decoupled from the coil system which generates a temporally variable magnetic field. Moreover, when use is made of a coil (but preferably of a plurality of coils), an improved signal-to-noise ratio can be obtained.

The amplitude of the signals induced in the coil system is higher as the position of the zero point of the field in the examination zone changes faster, that is, as the changing of the temporally variable magnetic field superposed on the magnetic gradient field is faster. However, from a technical point of view it is difficult to generate a temporally variable magnetic field whose amplitude suffices to shift the zero point of the field to each point of the examination zone and whose speed of variation is sufficiently high to generate signals of adequate amplitude. This problem is mitigated by the embodiment disclosed in claim 15 in which two magnetic fields which are variable at a different speed and with a different amplitude relative to one another are generated, that is, preferably by means of two coil systems. A further advantage is obtained in that the changes of the field may be so fast (for example, >20 kHz) that they are beyond the human limit of hearing.

The further embodiment as disclosed in claim 16 enables the shift of the field-free point in a two-dimensional zone. A second magnetic field, having a component extending perpendicularly to the two magnetic fields, enables extension to a three-dimensional zone.

The embodiment disclosed in claim 17 utilizes the fact that the magnetization characteristic is not linear in the zone in which the magnetization changes over from the non-saturated state to the saturated state. This non-linearity ensures that, for example, a magnetic field which varies sinusoidally in time at the frequency f causes a temporally variable induction of the frequency f (fundamental wave) and integer multiples of the frequency f (harmonic waves or higher harmonics) in the zone of non-linearity. The evaluation of the harmonic waves offers the advantage that the fundamental wave of the magnetic field which is active simultaneously with the shifting of the field-free point has no effect on the evaluation.

Figure 2:
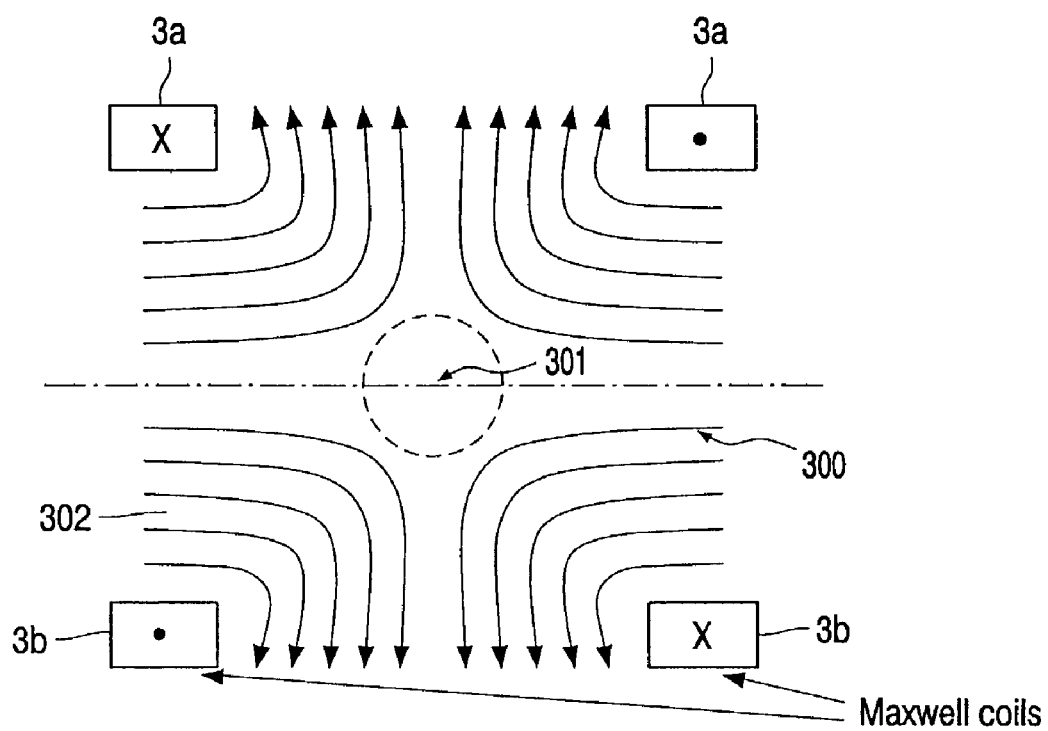
Figure 3:
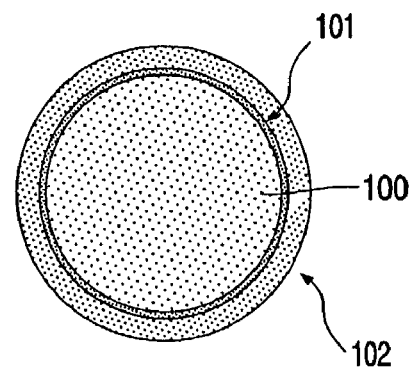
Figure 4A:
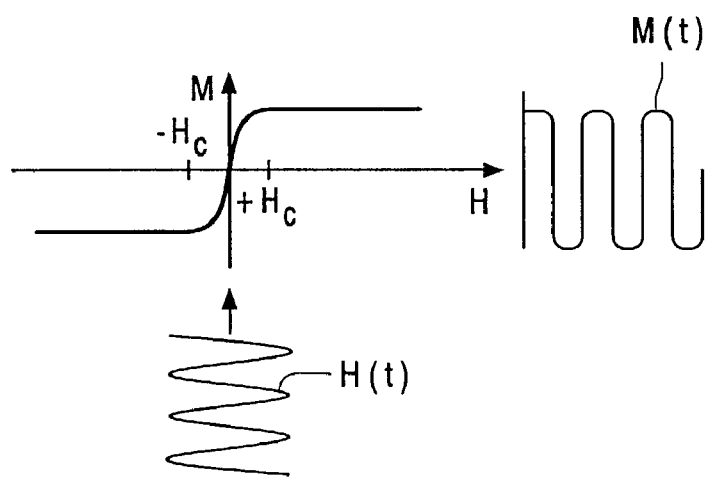
Figure 4B:
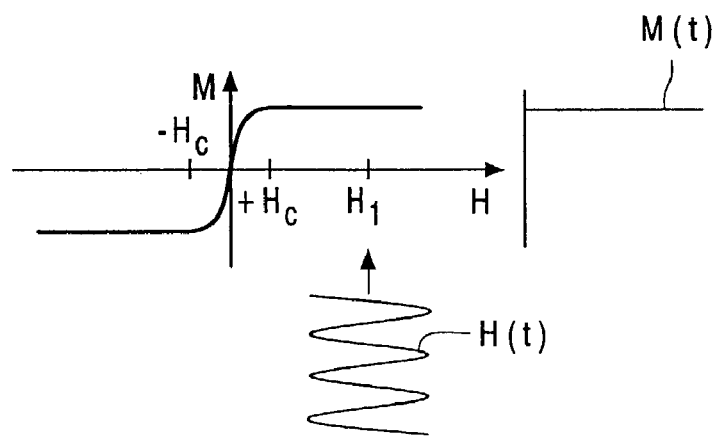
Figure 5:
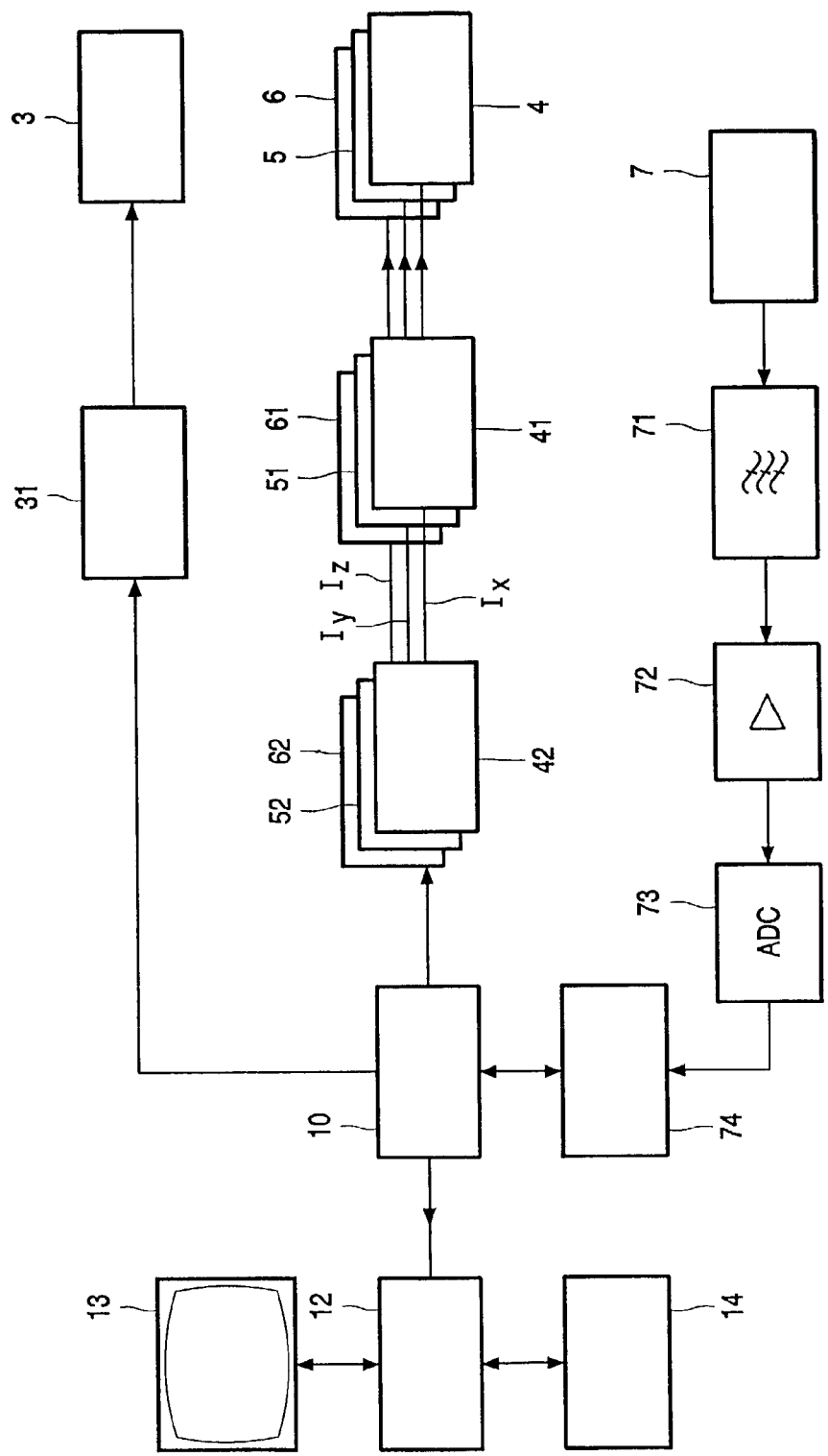
Figure 6A:
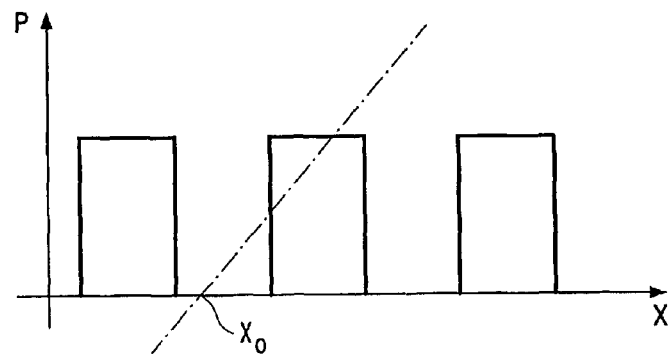
Figure 6B:
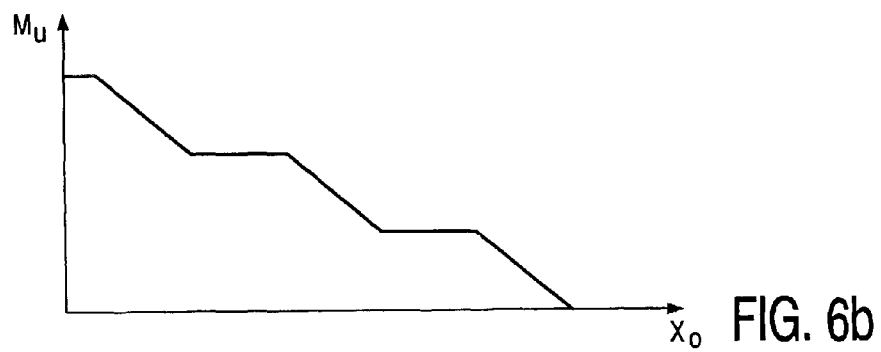
Figure 6C:
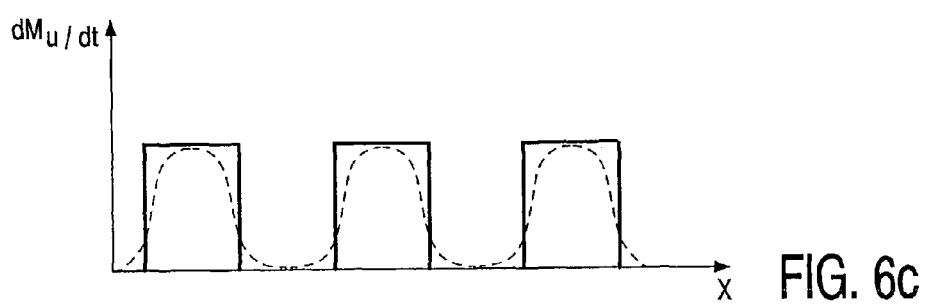
Figure 6D:
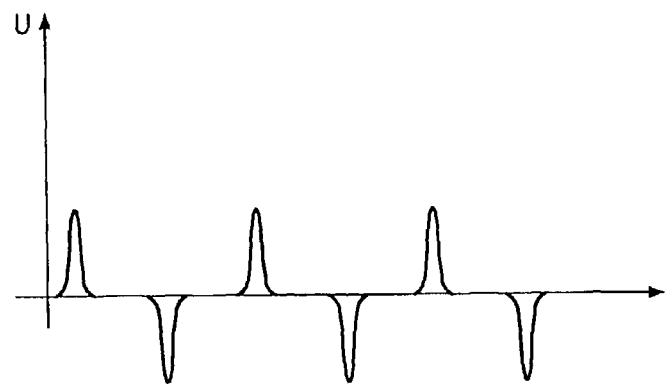
Figure 7:
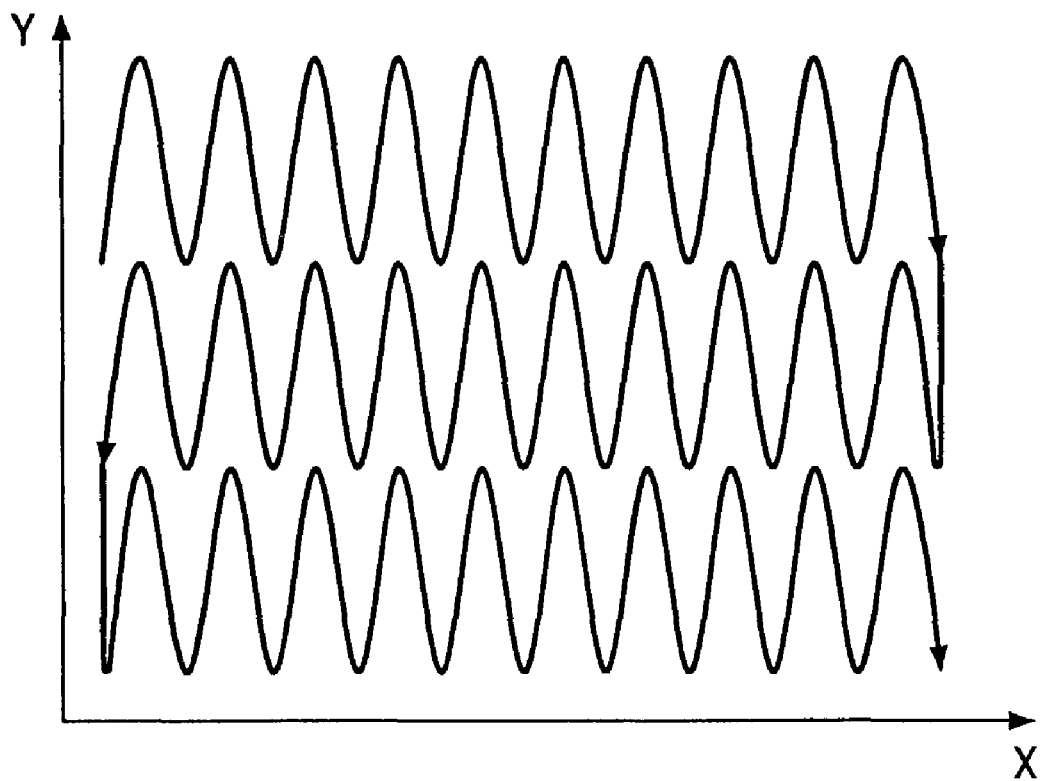

The invention will be described in detail hereinafter, by way of example, with reference to drawings. Therein:

FIG. 1 shows an apparatus for carrying out the method in accordance with the invention, FIG. 2 shows the field line pattern produced by a coil provided therein, FIG. 3 shows a magnetic particle which is present in the examination zone, FIG. 4 shows the magnetization characteristic of such particles, FIG. 5 shows a circuit diagram of the arrangement of FIG. 1, FIG. 6 shows the variation of various signals in the apparatus shown in the FIGS. 1 and 5, and FIG. 7 shows the shift of the field-free point in a two-dimensional zone.

FIG. 1 shows an object to be examined 1, in this case being a patient who is arranged on a patient table, only the top 2 of which is partly indicated. Prior to an examination, for example, of the gastrointestinal tract, a liquid or a meal with magnetic particles is administered to the patient 1.

A particle of this kind is shown in FIG. 3. It includes a spherical substrate 100, for example, of glass which is covered with a soft-magnetic layer 101 which has a thickness of, for example, 5 nm and consists, for example, of an iron nickel alloy (for example, permalloy). This layer may be covered, for example, with a cover layer 102 which protects the particle against acids. The strength of the magnetic field required for the saturation of the magnetization of such particles is dependent on their diameter. In the case of a diameter of 10 µm, a magnetic field of 1 mT is required whereas in the case of a diameter of 100 µm, a magnetic field of 100 µT suffices. When a coating of a material having a lower saturation magnetization is chosen, even lower values are achieved.

FIGS. 4a and 4b show the magnetization characteristic, that is, the variation of the magnetization M as a function of the field strength H, in a dispersion with such particles. It appears that the magnetization M no longer changes beyond a field strength $+H_c$ and below a field strength $-H_c$, meaning that saturated magnetization is obtained. The magnetization is not saturated between the values $+H_c$ and $-H_c$.

FIG. 4a illustrates the effect of a sinusoidal magnetic field H(t) if no further magnetic field is active. The magnetization changes between its saturation values at the rhythm of the frequency of the magnetic field H(t). The resultant variation in time of the magnetization is denoted by the reference M(t) in FIG. 4a. It can be seen that the magnetization also changes periodically, so that a like-wise periodic signal is induced outside the coil. Because of the non-linearity of the magnetization characteristic, this signal is no longer purely sinusoidal but contains harmonic waves, that is, higher harmonics of the sinusoidal fundamental wave. Such harmonic waves, which can be readily separated from the fundamental wave, are a measure of the particle concentration.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) then remains constant in time. Consequently, the magnetic field H(t) does not change the state of magnetization and does not cause a signal which could be detected by means of a suitable coil.

In order to extract information concerning the spatial concentration of the magnetic particles in the object 1 to be examined, a plurality of coil pairs are arranged above and underneath the patient 1 or the table top; the range of these coil pairs defines the examination zone (FIG. 1). A first coil pair 3 includes the two identically constructed windings 3a and 3b which are arranged coaxially above and underneath the patient and conduct equally large but oppositely directed currents. The gradient magnetic field thus generated is represented by the field lines 300 in FIG. 2. In the direction of the (perpendicular) axis of the coil pair it has a substantially constant gradient and in a point on this axis it reaches the value zero. Starting from this field-free point, the strength of the magnetic field increases in all three spatial directions as a function of the distance from this point. In a zone 301 which is denoted by a dashed line (the first sub-zone) around the field-free point the field strength is so low that the magnetization of magnetic particles present therein is not saturated, whereas the magnetization is in a state of saturation outside the zone 301. In the zone remaining outside the zone 301 (the second sub-zone 302) the magnetization of the particles is in the saturated state.

The size of the zone 301 determines the spatial resolution of the apparatus and is dependent on the one hand on the strength of the gradient of the gradient magnetic field and on the other hand on the strength of the magnetic field required for saturation. For a diameter of 10 µm of the sphere shown in FIG. 3 this strength amounts to 1 mT and to 100 µT for a diameter of 100 µm. For the latter value and a gradient of 0.2 T/m of the magnetic field, the zone 301 (in which the magnetization of the particles is not saturated) has a dimension of 1 mm.

When a further magnetic field is superposed on the gradient magnetic field in the examination zone, the zone 301 is shifted in the direction of this magnetic field, the extent of the shift being greater as the strength of the magnetic field is greater. When the superposed magnetic field is variable in time, the position of the zone 301 changes accordingly in time and in space.

In order to generate such temporally variable magnetic fields for any arbitrary direction in space, three further coil pairs are provided. The coil pair 4 with the windings 4a and 4b generates a magnetic field which extends in the direction of the coil axis of the coil pair 3a, 3b, that is, vertically. To this end, the two windings are supplied with equal currents which also flow in the same direction. The effect that can be achieved by means of this coil pair can in principle be achieved also by superposing currents flowing in the same direction on the oppositely directed equal currents in the coil pair 3a, 3b, so that the current in one coil pair decreases while it increases in the other coil pair. However, it may be advantageous when the temporally constant gradient magnetic field and the temporally variable vertical magnetic field are generated by separate coil pairs.

In order to generate magnetic fields which extend horizontally in space in the longitudinal direction of the patient and in a direction perpendicular thereto, there are provided two further coil pairs which include the windings 5a, 5b and 6a, 6b. If coil pairs of the Helmholz type, like the coil pairs 3a, 3b and 4a, 4b, were used for this purpose, these coil pairs would have to be arranged to the left and to the right of the examination zone and in front of and behind the examination zone, respectively. The accessibility of the examination zone would thus be impeded.

Therefore, the windings 5a, 5b and 6a, 6b of the coil pairs are also arranged above and underneath the examination zone, so that they must have a winding configuration other than that of the coil pair 4a, 4b. Coils of this kind, however, are known from magnetic resonance apparatus with an open magnet (open MRI) in which an RF coil pair is arranged above and underneath the examination zone so as to generate a horizontal, temporally variable magnetic field. Therefore, the construction of such coils need not be elaborated herein.

Finally, FIG. 1 also shows a further coil 7 which serves for the detection of signals generated in the examination zone. In principle any of the field generating coil pairs 3 to 6 could be used for this purpose. However, the use of a separate receiving coil offers advantages. A more attractive signal-to-noise ratio is obtained (notably when a plurality of receiving coils is used) and the coil can be arranged and switched in such a manner that it is decoupled from the other coils.

FIG. 5 shows a circuit diagram of the apparatus shown in FIG. 1. The coil pair 3 is shown diagrammatically (for the sake of simplicity, the indices a, b have been omitted for all coil pairs in FIG. 5) and receives a direct current from a controllable current source 31, which direct current can be switched on and off under the control of the control unit 10. The control unit 10 co-operates with a workstation 12 which includes a monitor 13 for the display of the images showing the distribution of the particles in the examination zone. A user can make entries via a keyboard or other input device 14.

The coil pairs 4, 5, 6 receive their currents from current amplifiers 41, 51 and 61. The variation in time of the currents $I_x$, $I_y$ and $I_z$ which are to be amplified and produce the desired magnetic fields is imposed by a respective waveform generator 42, 52 and 62. The waveform generators 42, 52, 62 are controlled by the control unit 10 which calculates the variation in time of the currents as required for the relevant examination method and loads this variation into the waveform generators. During the examination these signals are read from the waveform generators and applied to the amplifiers 41, 51, 61 which generate the currents required for the coil pairs 4, 5 and 6 on the basis thereof.

Generally speaking, a non-linear relationship exists between the shift of the zone 301 from its position at the center of the gradient coil system 3 and the current through the gradient coil system. Moreover, generally speaking, all three coils should generate a magnetic field when the zone 301 is to be shifted along a line extending outside the center. This fact is taken into account by the control unit while imposing the variation in time of the currents, for example, by means of suitable tables. The zone 301, therefore, can be shifted along arbitrarily formed paths through the examination zone.

The signals received by the coil 7 are applied to an amplifier 72 via a suitable filter 71. The output signals of the amplifier 72 are digitized by an analog-to-digital converter 73 so as to be applied to an image processing unit 74 which reconstructs the spatial distribution of the particles from the signals and the position each time occupied by the zone 301 during the reception of the signals.

A possibility for the acquisition of the signals required for the reconstruction of the concentration of the particles in a one-dimensional object extending in the z direction will be described in detail hereinafter with reference to FIG. 6. FIG. 6a shows the concentration P of the particles in the x direction. For the sake of simplicity it is assumed that there are three equally wide zones with the same particle concentration, which zones are separated from one another by zones without particles. It is also assumed that the magnetic field varies linearly in the x direction, as denoted by a dashed line, its direction being reversed at the point $x=x_0$ (at which point, therefore, the center of the zone 301 is situated each time). Finally, it is assumed that this point is shifted in the x direction at a constant speed.

FIG. 6b shows the overall magnetization $M_u$ in the examination zone as it results from the above assumptions. The overall magnetization is subject to the relation:

$$M_u = C \int_{-\infty}^{+\infty} f(x - x_o) P(x) dx \qquad (1)$$

Therein, C is a constant, P(x) is the concentration of the particles at the location x and $f(x-x_0)$ is a function which represents the spatial variation of the magnetization in the x direction in conformity with the magnetization characteristic (see FIGS. 4a and 4b). In the ideal case, that is, when the strength of the magnetic field required to saturate the magnetization tends towards zero, $f(x-x_0)=-1$ for $x<x_0$ and $+1$ for $x>x_0$.

The variation shown in FIG. 6b is thus obtained. The overall magnetization $M_u$ is then constant outside the zones in which particles are concentrated, and within these zones it varies in conformity with the integral over the particle concentration. Therefore, the particle concentration can be determined (by differentiation) from the spatial variation of the overall magnetization. The foregoing is subject to the condition that the overall magnetization is measured in an adequate number of positions $x_0$, for example, by means of a SQUID. A measurement of this kind would be very intricate.

The time derivative $dM_u/dt$ can be determined more readily than the overall magnetization, that is, by means of the receiving coil 7. In the ideal case the signal varies as a function of the location $x_0$ or (because of the constant speed of shifting) as a function of time, that is, as denoted by solid lines in FIG. 6c. Because of the non-ideal magnetization characteristic (that is, because the magnetic field first has to have a given strength before the particles become saturated), however, the variation as denoted by a dashed line is obtained. The sharp edges of the concentration profile are then no longer correctly represented by the signal received.

This undesirable variation is the result of the convolution of the magnetization M(x) with the function $f(x-x_0)$ in the equation 1. Because the function $f(x-x_0)$ is predetermined by the magnetic properties of the particles, the convolution operation in the image processing unit 74 (FIG. 5) can be compensated by reconvolution with this function. The variation denoted by solid lines in FIG. 6c would then be obtained even in the case of a non-ideal magnetization characteristic.

The signal induced in the coil 7 is greater as the magnetization in the examination zone is changed faster. However, it is difficult to shift the zone 301 quickly through the entire examination zone. It is possible, however, to superpose a temporally quickly, preferably sinusoidally variable magnetic field (for example, at a frequency of 200 kHz) on the magnetic field which varies spatially linearly (and slowly) and whose zero point $x_0$ is shifted in the x direction. The magnetization in the zone then changes in dependence on the superposed magnetic field as described in detail with reference to the FIGS. 4a and 4b.

The amplitude of the signal then induced in the coil 7 then varies as a function of the position (or time) as shown in FIG. 6d. It is only when the zone 301 is situated in the vicinity of the edges of the concentration profile that a significant signal amplitude occurs. This amplitude thus corresponds to the spatial derivative of the particle concentration. Therefore, in this case integration over the amplitude still has to be carried out in the image processing unit 74.

The sinusoidal magnetic field which causes the changing of the magnetization in the zone 301 is active simultaneously with this changing of the magnetization, that is, in the entire examination zone. If it is not ensured that the coil whereby the sinusoidal field is generated and the receiving coil 7 are inductively completely decoupled from one another, the temporally sinusoidal magnetic field always causes an (undesirable) sinusoidal component in the receiving coil 7, which component is superposed on the signal resulting from the changing of the magnetization in the zone 301. A further problem consists in that a signal from the zone 302 is also induced in the coil 7, because the magnetization characteristic is not ideal and exhibits a slope other than zero in the saturation range. This fact could be taken into account by subtracting a given value from the signal induced in the receiving coil 7.

This problem, however can be avoided by taking into account harmonic waves (higher harmonics of the fundamental wave) for evaluation instead of the fundamental wave with the frequency of the sinusoidal signal induced in the coil. This is because such higher harmonics can arise only in the zone 301 as a result of the non-linear magnetization characteristic of the particles. Therefore, the filter 71 (FIG. 5) is a high-pass filter or bandpass filter which transmits only the higher harmonics of the fundamental oscillation.

The shift of the zone 301 in the x direction only enables the determination of the spatial distribution of the particles in the z direction. In practice, however, this distribution is also to be determined in a two-dimensional or three-dimensional zone. To this end, on the magnetic field which changes the position of the zone 301 comparatively slowly in the x direction there is superposed a magnetic field which changes this position in the y direction periodically, for example, sinusoidally, that is, significantly faster but with a lower amplitude than in the x direction. When a given position is reached in the x direction, the shift in the x direction is reversed (so that the zone 301 is shifted back) and at the same time the sinusoidal field is changed by a constant value, so that the two-dimensional shift of the zone 3 through the examination zone is obtained as shown in FIG. 7. If a further component which shifts the magnetic field in the z direction is superposed on this field after each scan of the two-dimensional zone, the spatial distribution of the particles can be determined in a three-dimensional zone.

In the case of the three-dimensional scanning of the examination zone or a three-dimensional object, the equation (1) becomes $$M_u = \int_V f(r - r_0) P(r) dV \tag{2}$$

The quantities printed in heavy print are vectors: $M_u$ represents the vector of the overall magnetization, V denotes the examination zone, r and $r_0$ are the position vectors of an arbitrary point or the field-free point in the examination zone. $f(r-r_0)$ is a (vectorial) function which represents the spatial variation of the magnetization in conformity with the magnetization characteristic, and for which the following relation holds:

$$f(r-r_0) = f(|H(r)|) \cdot E(H(r)) \tag{3}$$

where H(r) is the magnetic field strength and E(H(r)) represents the unity vector in the direction of the magnetic field strength. The concentration P(r) of particles at the position r can be determined from the equation (2) by way of a reconvolution operation in the image processing unit 74 (FIG. 5).

If instead of only one component of the magnetization vector $M_u$ a component is determined in all three spatial directions in order to improve the reconstruction, (at least) one receiving coil which is capable of receiving the corresponding component is required for each direction.

The advantage of the method in accordance with the invention over magnetic resonance methods consist in that it does not require a magnet which generates a strong, spatially uniform magnetic field. The requirements imposed as regards the temporal stability and the linearity are significantly less severe than in the magnetic resonance method, so that the construction of such an apparatus can be significantly simpler than that of an MR apparatus. The requirements imposed as regards the variation in space of the magnetic field are also less severe, so that coils with "iron cores" (soft-magnetic core, for example iron) can also be used, so that they become more effective and smaller.

Instead of using the magnetic particles with a soft-magnetic coating as described with reference to FIG. 3, use can be made of so-called monodomain particles of ferromagnetic or ferrimagnetic material. These particles have dimensions in the nanometer range and are so small that no magnetic domains or Weiss zones can be formed therein. These particles can be injected into the blood stream of a patient in a suitable colloidal dispersion. Dispersions of this kind are already injected as a contrast agent in the field of MR. The magnetic particles used therein have dimensions of from 5 to 10 nm. This value is not yet optimal in the context of the invention. This is because the magnetic field strength required for saturation decreases as $1/d^3$, where d is the particle diameter. Therefore, the dimensions of such particles should be as small as possible, but not so large that magnetic domains can be formed therein. Depending on the magnetic material, the optimum size is in a range of between 20 and 800 nm.

The particles are enriched to a different extent in different types of tissue. This effect can also be used for diagnosis and can be further intensified by enclosing the particles by means of an envelope of organic molecules which enhance the biocompatibility and have given adhesion properties for enrichment on given biological structures. The imaging of the distribution of such particles enables so-called "molecular imaging".

Magnetic particles having a low effective anisotropy offer the advantage that, when the magnetization direction changes, the individual particle need not change its orientation because the magnetization vector inside the particle changes. In the case of particles having a higher effective anisotropy, the magnetization direction changes partly within the particle, but also partly because the particle becomes aligned in the direction of the magnetic field. This alignment is slow in comparison with the change of the magnetization direction within the particle, the speed of change being dependent on the viscosity of the medium in which the particle is present.

This aspect can be used to measure the viscosity (or the adhesion of the particles). To this end, the zone 301 is shifted at least twice at a different speed to a measuring point or measuring zone in which the viscosity is to be determined. The difference of the magnetization determined for the measuring point constitutes a measure of the viscosity and/or the adhesion. This effect can also be used for measuring the speed of the flow of a medium containing the particles, that is, by shifting the zone 301 at least twice from different directions to a measuring point or measuring range in which the flow speed is to be determined.

The method in accordance with the invention can also be carried out in combination with an MR examination, during which at least some of the coils present can be used for the reception of magnetic signals.

The invention claimed is:

1. A method of determining the spatial distribution of magnetic particles in an examination zone, which method comprises the acts of
  a) generating a magnetic field having a magnetic field strength which varies in space wherein a first sub-zone having a low magnetic field strength and a second sub-zone having a high magnetic field strength are formed in the examination zone, wherein the act of generating comprises acts of:
    providing a first substantially constant current in a first coil of a coil pair; and
    providing a second substantially constant current in a second coil of the coil pair, wherein the first current and the second current are substantially equal and oppositely directed currents, wherein but for other magnetic forces, the coil pair produces a temporally constant magnetic field,
  b) changing the position in space of the two sub-zones in the examination zone wherein the magnetization of the particles changes locally by inducing a spatially variable magnetic field into the magnetic field,
  c) acquiring signals which are dependent on the magnetization in the examination zone which has been influenced by the changing of the position in space, and
  d) evaluating the signals in order to extract information concerning the spatial distribution of the magnetic particles in the examination zone.

2. The method as claimed in claim 1, in which the spatially variable magnetic field is also a temporally variable magnetic field that is generated in order to change the position in space of the two sub-zones in the examination zone.

3. The method as claimed in claim 2, in which the signals induced in at least one coil as a result of the temporal variation of the magnetization in the examination zone are received and evaluated in order to extract information concerning the spatial distribution of the magnetic particles in the examination zone.

4. The method as claimed in claim 3, in which a temporally variable magnetic field in a first frequency band acts on the examination zone and a second frequency band, containing frequency components higher than those of the first frequency band, of the signal received in the coil is evaluated in order to extract information concerning the spatial distribution of the magnetic particles.

5. The method as claimed in claim 1, wherein multidomain particles of ferromagnetic or ferrimagnetic material are introduced into the examination zone.

6. The method as claimed in claim 5, wherein substrates which have dimensions in the μm range and are provided with a thin layer of a ferromagnetic soft material are utilized as the multidomain particles.

7. A method of determining the spatial distribution of magnetic particles in an examination zone, which method comprises the acts of
  a) introducing monodomain particles of ferromagnetic or ferrimagnetic material into the examination zone,
  b) generating a magnetic field having a magnetic field strength which varies in space wherein a first sub-zone having a low magnetic field strength and a second sub-zone having a high magnetic field strength are formed in the examination zone,
  c) changing the position in space of the two sub-zones in the examination zone wherein the magnetization of the particles changes locally,
  d) acquiring signals which are dependent on the magnetization in the examination zone which has been influenced by the changing of the position in space, and
  e) evaluating the signals in order to extract information concerning the spatial distribution of the magnetic particles in the examination zone.

8. The use of the particles as claimed in claim 7 in a colloidal dispersion.

9. An arrangement for determining the spatial distribution of magnetic particles in an examination zone, the arrangement comprising
  a) means for generating a magnetic field having a magnetic field strength which varies in space wherein a first sub-zone having a low magnetic field strength and a second sub-zone having a high magnetic field strength are formed in the examination zone, wherein the means for generating comprises:
    a first coil of a coil pair having a first substantially constant current; and
    a second coil of the coil pair having a second substantially constant current, wherein the first current and the second current are substantially equal and oppositely directed currents, wherein but for other magnetic forces, the coil pair produces a temporally constant magnetic field,
  b) means for changing the position in space of the two sub-zones in the examination zone wherein the magnetization of the particles changes locally by inducing a spatially variable magnetic field into the magnetic field,
  c) means for the acquisition of signals which are dependent on the magnetization in the examination zone which has been influenced by the changing of the position in space, and
  d) means for evaluating the signals in order to extract information concerning the spatial distribution of the magnetic particles in the examination zone.

10. The arrangement as claimed in claim 9, in which the means for generating the magnetic field comprise a gradient coil system for generating a magnetic gradient field whose direction is reversed in the first sub-zone of the examination zone and which comprises a zero crossing.

11. The arrangement as claimed in claim 9, comprising a coil system for receiving signals induced by the spatial variation of the magnetization in the examination zone.

12. An arrangement for determining the spatial distribution of magnetic particles in an examination zone, the arrangement comprising
  a) means for generating a magnetic gradient field having a magnetic field strength which varies in space wherein a first sub-zone having a low magnetic field strength and a second sub-zone having a high magnetic field strength are formed in the examination zone,
b) means for generating a temporally variable magnetic field which is superposed on the magnetic gradient field and serves to displace the two sub-zones in the examination zone for changing the position in space of the two sub-zones in the examination zone wherein the magnetization of the particles changes locally,
c) means for the acquisition of signals which are dependent on the magnetization in the examination zone which has been influenced by the changing of the position in space,
d) means for evaluating the signals in order to extract information concerning the spatial distribution of the magnetic particles in the examination zone.

13. An arrangement for determining the spatial distribution of magnetic particles in an examination zone, the arrangement comprising
a) means for generating a magnetic gradient field having a magnetic field strength which varies in space wherein a first sub-zone having a low magnetic field strength and a second sub-zone having a high magnetic field strength are formed in the examination zone,
b) means for changing the position in space of the two sub-zones in the examination zone wherein the magnetization of the particles changes locally,
c) means for the acquisition of signals which are dependent on the magnetization in the examination zone which has been influenced by the changing of the position in space,
d) means for evaluating the signals in order to extract information concerning the spatial distribution of the magnetic particles in the examination zone, and
e) means for generating a first and at least a second magnetic field which is superposed on the magnetic gradient field, the first magnetic field being relatively slowly variable in time with a high amplitude with regard to the second magnetic field, while the second magnetic field is relatively quickly variable in time with a low amplitude with regard to the first magnetic field.

14. The arrangement as claimed in claim 13, in which the two magnetic fields in the examination zone extend essentially perpendicularly to one another.

15. An arrangement for determining the spatial distribution of magnetic particles in an examination zone, the arrangement comprising
a) means for generating a magnetic gradient field having a magnetic field strength which varies in space wherein a first sub-zone having a low magnetic field strength and a second sub-zone having a high magnetic field strength are formed in the examination zone,
b) means for changing the position in space of the two sub-zones in the examination zone wherein the magnetization of the particles changes locally,
c) means for the acquisition of signals which are dependent on the magnetization in the examination zone which has been influenced by the changing of the position in space,
d) means for evaluating the signals in order to extract information concerning the spatial distribution of the magnetic particles in the examination zone, which arrangement comprises a filter which succeeds the coil system and suppresses the signal components in a first frequency band in the signal induced in the coil system and transmits the signal components in a second frequency band which contains frequency components which are higher than those of the first frequency band.

16. A method of determining the spatial distribution of magnetic particles in an examination zone, which method comprises the acts of
generating a magnetic field having a magnetic field strength which varies in space wherein a first sub-zone having a low magnetic field strength and a second sub-zone having a high magnetic field strength are formed in the examination zone,
changing the position in space of the two sub-zones in the examination zone wherein the magnetization of the particles changes locally by inducing a spatially variable magnetic field into the magnetic field,
acquiring signals which are dependent on the magnetization in the examination zone which has been influenced by the changing of the position in space, and
evaluating the signals in order to extract information concerning the spatial distribution of the magnetic particles in the examination zone, wherein the spatially variable magnetic field is also a temporally variable magnetic field that is generated in order to change the position in space of the two sub-zones in the examination zone, wherein the signals induced in at least one coil as a result of the temporal variation of the magnetization in the examination zone are received and evaluated in order to extract information concerning the spatial distribution of the magnetic particles in the examination zone, and wherein a temporally variable magnetic field in a first frequency band acts on the examination zone and a second frequency band, containing frequency components higher than those of the first frequency band, of the signal received in the coil is evaluated in order to extract information concerning the spatial distribution of the magnetic particles.

17. An arrangement for determining the spatial distribution of magnetic particles in an examination zone, the arrangement comprising
means for generating a magnetic field having a magnetic field strength which varies in space wherein a first sub-zone having a low magnetic field strength and a second sub-zone having a high magnetic field strength are formed in the examination zone,
means for changing the position in space of the two sub-zones in the examination zone wherein the magnetization of the particles changes locally by inducing a spatially variable magnetic field into the static magnetic field,
means for the acquisition of signals which are dependent on the magnetization in the examination zone which has been influenced by the changing of the position in space, and
means for evaluating the signals in order to extract information concerning the spatial distribution of the magnetic particles in the examination zone, wherein the means for generating the magnetic field comprise a gradient coil system for generating a magnetic gradient field whose direction is reversed in the first sub-zone of the examination zone and which comprises a zero crossing.

* * * * *